United States Patent [19]

Dills et al.

[11] Patent Number: 4,992,276

[45] Date of Patent: Feb. 12, 1991

[54] ANTISEPTIC COMPOSITIONS CONTAINING HEXAHYDRO-5-PYRIMIDINAMINE COMPOUNDS AND THYMOL AND METHODS FOR PREPARING SAME

[75] Inventors: Steven S. Dills, Hackettstown; Deborah A. Noonan, Florham Park, both of N.J.

[73] Assignee: Warner-Lambert Company, Morris Plains, N.J.

[21] Appl. No.: 284,213

[22] Filed: Dec. 14, 1988

[51] Int. Cl.$^5$ .............................................. A61K 47/00
[52] U.S. Cl. ..................................... 424/439; 424/49; 424/54
[58] Field of Search ........................... 424/439, 49, 54

[56] References Cited

U.S. PATENT DOCUMENTS

| | | | |
|---|---|---|---|
| 4,029,760 | 6/1977 | Holtzhauer et al. | 424/49 |
| 4,522,806 | 6/1985 | Muhlemann et al. | 424/54 |
| 4,666,517 | 5/1987 | Bakar | 424/52 |
| 4,713,243 | 12/1987 | Schiraldi et al. | 424/449 |
| 4,719,100 | 1/1988 | Frosch | 424/49 |
| 4,774,078 | 9/1988 | Curtis et al. | 424/49 |
| 4,795,628 | 1/1989 | Afseth | 424/49 |

Primary Examiner—Thurman K. Page
Assistant Examiner—P. L. Prater
Attorney, Agent, or Firm—Carl W. Battle; Gary M. Nath

[57] ABSTRACT

The present invention pertains to oral antiseptic compositions comprising a therapeutically effective amount of a synergistic antiseptic composition comprising an antiseptic hexahydro-5-pyrimidinamine compound and thymol in an oral vehicle or in a pharmaceutically acceptable carrier such as a confectionery bulking agent. The synergistic antiseptic compositions may be utilized in a wide variety of aqueous-based oral antiseptic products and confectionery products. This invention also relates to methods by which these oral antiseptic and confectionery products may be prepared.

15 Claims, No Drawings

ANTISEPTIC COMPOSITIONS CONTAINING HEXAHYDRO-5-PYRIMIDINAMINE COMPOUNDS AND THYMOL AND METHODS FOR PREPARING SAME

BACKGROUND OF THE INVENTION

1. Field of the Invention

This invention pertains to novel oral antiseptic compositions useful in promoting oral hygiene. The novel compositions are prepared by combining a therapeutically effective amount of a synergistic antiseptic composition comprising a hexahydro-5-pyrimidinamine compound and thymol in an oral vehicle or in a pharmaceutically acceptable carrier such as a confectionery bulking agent. Such oral antiseptic compositions are useful against the bacteria most commonly associated with the formation of dental plaque and caries such as *Streptococcus sanguis* and *Streptococcus mutans*, respectively. The synergistic antiseptic compositions may be utilized in a wide variety of aqueous-based oral antiseptic products and confectionery products. This invention also relates to methods by which these oral antiseptic and confectionery products may be prepared.

2. Description of the Prior Art

Hexahydro-5-pyrimidinamine compounds (5-aminohexahydropyrimidine), such as hexetidine, which is also known as 1,3-bis(2-ethylhexyl)-hexahydro-5-methyl-5-pyrimidinamine, are well known in the art for their broad spectrum antimicrobial activity. These hexahydro-5-pyrimidinamine compounds are used in aqueous-based oral compositions for the treatment of oral infections such as gingivitis, oral ulcers, periodontal disease, and for the control of mouth odor.

Hexetidine is a saturated pyrimidine derivative which is soluble in most organic solvents and practically insoluble in water. The use of hexetidine at therapeutic levels, as the free base or salt, has many organoleptic disadvantages. These disadvantages include, for example, brown staining of dental enamel and bitter taste. Significant effort has been expended towards overcoming these undesirable side effects.

U.S. Pat. No. 2,837,463, issued to Fondick et al. and assigned to Warner-Lambert Company, discloses therapeutic compositions which comprise certain hexahydro-5-pyrimidinamine compounds and a pharmaceutical carrier. The hexahydro-5-pyrimidinamine compound may be hexetidine and the therapeutic compositions may contain optional additives such as menthol to add flavor.

U.S. Pat. No. 4,141,968, issued to Kunz et al. and assigned to Doll GmbH, West Germany, discloses the preparation and use of certain substituted benzoic acid salts of hexetidine, particularly the terephthalic acid and 4-sulfamylbenzoic acid salts. These salts are said to have useful bacteriostatic activity. The benzoic acid salt component may be monosubstituted or disubstituted. The substituent groups on benzoic acid are selected from the group consisting of -COOH, -OH, -NH$_2$, -SO$_3$H and -SO$_2$NH. When the substituent group is -COOH or -OH, the group must be located in the 4-position (para) on the benzoic acid moiety. When the benzoic acid salt component is disubstituted, the substituent groups must be different from each other. Substituent groups located at the 4-position on the benzoic acid ring are particularly preferred. Examples of the preferred substituted benzoic acid salts of hexetidine include:

1,3-bis(2-ethylhexyl)hexahydro-5-methyl-5-pyrimidinamine terephthalate 1,3-bis(2-ethylhexyl)hexahydro-5-methyl-5-pyrimidinamine 4-sulfamylbenzoate 1,3-bis(2-ethylhexyl)hexahydro-5-methyl-5-pyrimidinamine 4-hydroxybenzoate 1,3-bis(2-ethylhexyl)hexahydro-5-methyl-5-pyrimidinamine 2-aminobenzoate 1,3-bis(2-ethylhexyl)hexahydro-5-methyl-5-pyrimidinamine 4-aminobenzoate 1,3-bis(2-ethylhexyl)hexahydro-5-methyl-5-pyrimidinamine 4-aminosalicylate 1,3-bis(2-ethylhexyl)hexahydro-5-methyl-5-pyrimidinamine 5-sulfosalicylate U.S. Pat. No. 4,206,198, issued to Schmolka and assigned to BASF Wyandotte Corporation, discloses a dentifrice composition which contains a foam producing amount of a nonionic surfactant and a cationic antidecay agent. The nonionic surfactant is an ethoxylated adduct of a C-15 or C-16 fatty alcohol. The cationic antidecay agent may be hexetidine and the dentifrice composition may contain optional flavoring additives such as eucalyptus and sodium methylsalicylate.

U.S. Pat. No. 4,323,552, issued to Schmolka and assigned to BASF Wyandotte Corporation, discloses a high foaming dentifrice gel composition said to be compatible with antimicrobial agents. The gel composition comprises a nonionic surfactant and a cationic antidecay agent. The nonionic surfactant is a cogeneric mixture of conjugated polyoxybutylenepolyoxyethylene polymeric compounds with the polyoxybutylene polymers in the mixture having an average molecular weight of at least 500. The cationic antidecay agent may be hexetidine and optional flavoring additives such as eucalyptus and sodium methylsalicylate may be included in the high foaming dentifrice gel composition.

U.S. Pat. No. 4,343,785, issued to Schmolka and assigned to BASF Wyandotte Corporation, discloses a gel dentifrice composition said to retains its gel properties at low temperatures. The gel dentifrice contains about 15% of a cogeneric mixture of conjugated polyoxybutylene-polyoxyethylene block copolymers, an effective amount of an essential additive and less than about 85% water. The average molecular weight of the polyoxybutylene polymers in the mixture is at least 1200. Additional requirements relate the hydrophobic molecular weight of the polyoxybutylenepolyoxyethylene block copolymers to the minimum polyethylene content and the minimum block copolymer content. The essential additive in the gel dentifrice composition may be hexetidine and optional flavoring agents such as eucalyptus and sodium methylsalicylate may be included in the gel.

U.S. Pat. No. 4,522,806, issued to Muhlemann et al. and assigned to Lever Brothers Company, discloses an antiplaque composition which contains the combination of hexetidine, as the water-insoluble pyrimidine base, plus one or more zinc cationic salts. The antiplaque composition is said not to stain teeth.

U.S. Pat. No. 4,574,081, issued to Shymon and assigned to Colgate-Palmolive Company, discloses an antiplaque dentifrice having an improved flavor comprising an antiplaque compound, which may be hexetidine, a flavoring agent which consists essentially of at least 15% anethol, up to 46% menthol, up to 39% peppermint, and a sweetening agent in a dental vehicle containing a dental abrasive.

U.S. Pat. No. 4,624,849, issued to Toogood and assigned to The Proctor & Gamble Company, discloses a noncariogenic therapeutic lozenge comprising a cationic antimicrobial agent and a nonionic lubricant in a pharmaceutically acceptable carrier. The antimicrobial agent may be hexetidine and the lubricant is selected from the group consisting of polyethylene glycols, hydrogenated tallow and hydrogenated vegetable oil.

U.S. Pat. No. 4,666,517, issued to Bakar and assigned to Colgate-Palmolive Company, discloses an oral antiplaque and antigingivitis composition comprising a synergistic antiseptic combination of hexetidine and tridecanol-1, in the weight ratio of 1:1 to 5:1, respectively.

British patent no. 1,468,557, assigned to Societe Norgan, discloses a pharmaceutical composition said to prolong the antibacterial effect of hexetidine. The composition contains hexetidine, choline salicylate and chlorobutanol in a pharmaceutically acceptable solvent.

While the above hexetidine containing oral antiseptic compositions provide some degree of improved oral antiseptic activity, none of the above compositions can maintain a high level of efficacy without the disadvantages characteristic of hexahydro-5-pyrimidinamine compounds. Thus it would be commercially advantageous to be able to enhance or potentiate the antiseptic activity of hexahydro-5-pyrimidinamine compounds, such as hexetidine. By increasing the antiseptic activity of the hexahydro-5-pyrimidinamine compound, an antiseptic product could contain less of the antiseptic compound and thus have reduced side effects without a concomitant decrease in therapeutic benefits. The present invention provides such improved oral antiseptic compositions without the disadvantages characteristic of previously known products. The present invention also provides methods by which these improved oral antiseptic compositions may be prepared.

SUMMARY OF THE INVENTION

The present invention pertains to oral antiseptic compositions comprising a therapeutically effective amount of a synergistic antiseptic composition comprising an antiseptic hexahydro-5-pyrimidinamine compound and thymol in an oral vehicle or in a pharmaceutically acceptable carrier such as a confectionery bulking agent. The synergistic antiseptic compositions may be utilized in a wide variety of aqueous-based oral antiseptic products and confectionery products. This invention also relates to methods by which these oral antiseptic and confectionery products may be prepared.

DETAILED DESCRIPTION OF THE INVENTION

The present invention pertains to improve oral antiseptic compositions and a method for promoting oral hygiene. More specifically, the present invention pertains to novel oral antiseptic compositions useful in promoting oral hygiene and prepared by combining a therapeutically effective amount of a synergistic antiseptic composition comprising a hexahydro-5-pyrimidinamine compound and thymol in an oral vehicle or a pharmaceutically acceptable carrier such as a confectionery bulking agent. The synergistic antiseptic compositions may be utilized in a wide variety of aqueous-based oral antiseptic products and confectionery products. This invention also relates to methods by which these oral antiseptic and confectionery products may be prepared.

A method is provided for improving oral hygiene which includes applying to the oral cavity, and contacting the teeth with, an oral antiseptic composition comprising a synergistic antiseptic composition comprising a hexahydro-5-pyrimidinamine compound and thymol in an oral vehicle or a pharmaceutically acceptable carrier in an amount sufficient to inhibit the growth of Streptococcus mutans and Streptococcus sanguis in the oral cavity, in general, or on teeth, in particular.

In carrying out the method of the invention, the synergistic antiseptic combination of a hexahydro-5-pyrimidinamine compound and thymol will usually be employed in conjunction with a non-toxic oral vehicle carrier or a pharmaceutically acceptable carrier to prepare a wide variety of oral antiseptic compositions including oral and ingestible compositions. Oral compositions comprise compositions employing an oral vehicle which are intended to be taken by mouth but are not intended to be ingested such as, for instance, hygienic products like mouthwashes, rinses, oral sprays, dental gels and the like. Ingestible compositions comprise compositions employing pharmaceutically acceptable carriers such as confectionery bulking agents which are edible or partly edible and which are intended to be swallowed such as, for instance, lozenges, tablets, toffee, nougat, suspensions, chewy candy, chewing gum and the like.

The synergistic antiseptic compositions of the present invention are present in the oral antiseptic compositions in therapeutically effective amounts. These amounts are readily determined by those skilled in the art without the need for undue experimentation. In a preferred embodiment, the oral antiseptic compositions comprise in percentages by weight (1) a hexahydro-5-pyrimidinamine compound in an amount from about 0.01% to about 0.3%, and (2) thymol in an amount from about 0.01% to about 0.4%. In a more preferred embodiment, the oral antiseptic compositions comprise in percentages by weight (1) a hexahydro-5-pyrimidinamine compound in an amount from about 0.05% to about 0.2%, and (2) thymol in an amount from about 0.05% to about 0.1%. In a most preferred embodiment, the oral antiseptic compositions comprise in percentages by weight (1) a hexahydro-5-pyrimidinamine compound in an amount from about 0.1% to about 0.15%, and (2) thymol in an amount from about 0.06% to about 0.08%. The oral vehicle or pharmaceutically acceptable carrier is present in a quantity sufficient to bring the total amount of the composition to 100%.

Any non-toxic, antiseptic hexahydro-5-pyrimidinamine compound or pharmaceutically acceptable salt thereof may be employed in the present invention. Suitable non-toxic, antiseptic hexahydro-5-pyrimidinamine compounds and pharmaceutically acceptable salts thereof are disclosed in U.S. Pat. Nos. 2,837,463 and 4,141,968, which disclosures are incorporated herein by reference. The preferred antiseptic hexahydro-5pyrimidinamine compound is hexetidine, and pharmaceutically acceptable salts thereof. The preferred pharmaceutically acceptable acid addition salts of hexetidine are the terephthalate, 4-sulfamylbenzoate, 4-hydroxybenzoate, 2-aminobenzoate, 4-aminobenzoate, 4-aminosalicylate, and 5-sulfosalicylate salts, and the like and mixtures thereof .

Thymol, also known as 5-methyl-2-(1-methylethyl)-phenol, is obtained from the essential oil of *Thymus vulgari L.* and *Monarda punctata L., Labiataer*. Essential oils are generally volatile oils derived from plants and usually carry the odor or flavor of the plant. Thymol is a white crystalline powder with an aromatic odor and taste and is soluble in organic solvents and only slightly soluble in water.

The synergistic antiseptic compositions of the present invention are prepared by admixing the hexahydro-5-pyrimidinamine compound and thymol.

The essence of the present invention is the synergistic antibacterial effect of inhibiting the growth of bacteria, such as *Streptococcus mutans* and *Streptococcus sanguis*, which is achieved when a therapeutic amount of a synergistic antiseptic combination of a hexahydro-5-pyrimidinamine compound and thymol in a suitable vehicle is employed in the oral cavity. The superior antiseptic properties are markedly greater than that expected by mere combination of the synergistic antiseptic components. Accordingly, the amount of dental staining and other disadvantages associated with the use of hexahydro-5-pyrimidinamine compounds is reduced or eliminated.

The synergistic antiseptic composition once prepared may be stored for future use or may be formulated with conventional additives such as oral vehicles and pharmaceutically acceptable carriers such as confectionery bulking agents to prepare a wide variety of oral antiseptic compositions to suit particular applications. Compositions employing an oral vehicle may be in the form of a mouthwash, rinse, oral spray, dental gel and the like. Compositions employing a pharmaceutically acceptable carrier such as a confectionery bulking agent may be in the form of a lozenge, tablet, toffee, nougat, suspension, chewy candy, chewing gum and the like.

In one form of the invention, the oral antiseptic composition includes an oral vehicle and is in the form of a liquid such as a mouthwash, rinse or oral spray. Generally an oral antiseptic mouthwash (or rinse) product in the present invention will contain, in percentages by weight, from about 0.025% to about 0.1% of a hexahydro-5-pyrimidinamine compound, with about 0.1% being preferred. An oral antiseptic spray in the present invention will generally contain, in percentages by weight, from about 0.05% to about 0.3% of a hexahydro-5-pyrimidinamine compound, with about 0.2% being preferred.

Typical non-toxic oral carrier vehicles known in the dental art may be used in the present invention. Preferred vehicles include water and water-alcohol mixtures. The water-alcohol mixtures are generally employed in a weight ratio from about 1:1 to about 20:1, preferably from about 3:1 to about 20:1, and most preferably from about 3:1 to about 10:1, respectively. The pH value of the vehicle is generally from about 4 to about 7, and preferably from about 5 to about 6.5. A vehicle having a pH value below about 4 is generally irritating to the oral cavity. A vehicle having a pH value greater than about 7 generally results in an unpleasant mouth feel.

The mouthwashes and sprays of the present invention may contain conventional additives normally employed in liquid oral antiseptic compositions. These additives include sorbitol solution, a surfactant, a fluorine providing compound, a sweetening agent, a flavoring agent, a coloring agent, a humectant, a buffer, and the like, providing the additives do not interfere with the antiseptic properties of the hexahydro-5-pyrimidinamine compound.

The liquid oral antiseptic composition of the present invention may contain sorbitol or sorbitol solution in high weight to volume concentrations (w/v), i.e., from about 25% to about 75% w/v, and preferably from about 50% to about 60% w/v, of sorbitol solution, U.S. Pharmacopeia, which is a solution of sorbitol in water containing 70% total solids. Sorbitol solution supplies sweetness and body to the composition and gives a desirable mouth feel. Sorbitol solution also enhances flavor, prevents harsh taste and provides a fresh and lively sensation in the mouth.

Surfactants (surface active agents) are organic compounds which reduce surface tension between liquids and aid in the dispersion of a composition throughout the oral cavity. The surfactant in the present invention may be nonionic, ampholytic, or cationic. The liquid oral antiseptic compositions of the present invention may contain surfactants in amounts up to about 5%, and preferably from about 0.05% to about 2%, by weight of the oral liquid antiseptic composition.

Suitable nonionic surfactants in the present invention include poly(oxyethylene)-poly(oxypropylene) block copolymers. Such copolymers are known commercially by the non-proprietary name of poloxamers, which name is used in conjunction with a numeric suffix to designate the individual identification of each copolymer. Poloxamers may have varying contents of ethylene oxide and propylene oxide which results in poloxamers which have a wide range of chemical structures and molecular weights. The nonionic poloxamer surfactants of the present invention are non-toxic, are acceptable as direct food additives, are stable, readily dispersible in aqueous. systems and are compatible with the wide variety of formulating ingredients used in oral compositions.

Poloxamer surfactants in the present invention should have a Hydrophilic-Lipophilic Balance (HLB) of between about 10 and about 30, and preferably between about 10 and about 25. Suitable poloxamers in this invention include: Poloxamers 105, 108, 123, 124, 183, 184, 185, 188, 215, 217, 234, 235, 237, 238, 284, 288, 334, 335, 338, and 407. A particularly preferred poloxamer is Poloxamer 407, which has an HLB of about 22, and is sold under the tradename Pluronic F-127 by BASF-Wyandotte, Parsippany, N.J. When present in the liquid oral antiseptic composition, poloxamers should constitute from about 0.2% to about 2%, and preferably from about 0.5% to about 1%, by weight of the total volume of liquid oral antiseptic composition (w/v).

Another class of nonionic surfactants useful in this invention are the ethoxylated hydrogenated castor oils. These surfactants are prepared by hydrogenating castor oil and treating the hydrogenated product with from about 10 to about 200 moles of ethylene glycol. These ethoxylated hydrogenated castor oils are known by the non-proprietary name of PEG hydrogenated castor oils, in accordance with the dictionary of the Cosmetics, Toiletries and Fragrance Association, 3rd Edition, which name is used in conjunction with a numeric suffix to designate the degree of ethoxylation of the hydrogenated castor oil product, i.e., the number of moles of ethylene oxide added to the hydrogenated castor oil product. Suitable PEG hydrogenated castor oils include PEG 16, 20, 25, 30, 40, 50, 60, 80, 100, and 200. In a preferred embodiment, the PEG hydrogenated castor oil surfactant is Cremophor RH40, a commercially available product from BASF-Wyandotte, Parsippany, N.J. Ethoxylated hydrogenated castor oil surfactants, when present in the liquid oral antiseptic composition, should constitute from about 0.2% to about 2%, and preferably from about 0.5% to about 1%, by weight of the total volume of liquid oral antiseptic composition (w/v).

Other nonionic surfactants useful in the present invention include condensates of sorbitan esters of fatty acids with ethylene oxide (polysorbates) such as sorbitan mono-oleate with from about 20 to about 60 moles of ethylene oxide (e.g., "Tweens," a trademark of ICI U.S., Inc.) Particularly preferred polysorbates are Polysorbate 20 (polyoxyethylene 20 sorbitan monolaurate, Tween 20) and Polysorbate 80 (polyoxyethylene 20 sorbitan mono-oleate, Tween 80).

Additional suitable nonionic surfactants useful in the present invention are the condensation products of an alpha-olefin oxide containing 10 to 20 carbon atoms, a polyhydric alcohol containing 2 to 10 carbon atoms and 2 to 6 hydroxyl groups, and either ethylene oxide or a mixture of ethylene oxide and propylene oxide. The resultant surfactants are polymers which have a molecular weight in the range from about 400 to about 1600, contain from about 40% to about 80% ethylene oxide, by weight, and have an alpha-olefin oxide to polyhydric alcohol mole ratio in the range from about 1:1 to about 1:3, respectively.

Other nonionic surfactants useful in the present invention include condensates of sorbitan esters of fatty acids with polyethylene glycol such as sorbitan diisostearate condensed with polyethylene glycol. A particularly preferred polyethylene glycol condensate of a diisostearate sorbate ester is EmSorb 2726, a commercially available product manufactured by Emery Industries Incorporated, Linden, N.J.

Amphoteric surfactants have the capacity to behave as either an acid or a base. Amphoteric surfactants useful in the present invention include quaternized imidazole derivatives.

Cationic surfactants are surfactants which carry a positive charge. Cationic surfactants useful in the present invention include cetypyridinium chloride.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the instant liquid oral antiseptic composition is dependent upon the type of fluorine providing compound employed, the solubility of the fluorine compound, and the nature of the final liquid oral antiseptic composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the oral liquid antiseptic composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof. Without being limited to particular sweetening agents, representative categories and examples include:

(a) water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), known, for example, under the product designation of Sucralose; and (e) protein based sweeteners such as thaumaoccous danielli (Thaumatin I and II).

In general, an effective amount of sweetening agent is utilized to provide the level of sweetness desired in the particular liquid oral antiseptic composition, and this amount will vary with the sweetener selected and the final oral antiseptic product. The amount of sweetener normally present is in the range from about 0.0025% to about 90%, by weight of the liquid oral antiseptic composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed and the like.

The amount of flavoring agent employed herein is normally a matter of preference subject to such factors as the type of final liquid oral antiseptic composition, the individual flavor employed, and the strength of flavor desired. Thus, the amount of flavoring may be varied in order to obtain the result desired in the final product and such variations are within the capabilities of those skilled in the art without the need for undue experimentation. The flavoring agents, when used, are generally utilized in amounts that may, for example, range in amounts from about 0.05% to about 6%, by weight of the liquid oral antiseptic composition.

The coloring agents (colors, colorants) useful in the present invention are used in amounts effective to produce the desired color. These coloring agents include pigments which may be incorporated in amounts up to about 6%, by weight of the liquid oral antiseptic composition. A preferred pigment, titanium dioxide, may be incorporated in amounts up to about 2%, and preferably less than about 1%, by weight of the composition. The colorants may also include natural food colors and dyes suitable for food, drug and cosmetic applications. These colorants are known as F. D. & C. dyes and lakes. The materials acceptable for the foregoing uses are preferably water-soluble. Illustrative nonlimiting examples include the indigoid dye known as F. D. & C. Blue No.2, which is the disodium salt of 5,5-indigotindisulfonic acid. Similarly, the dye known as F. D. & C. Green No.1 comprises a triphenylmethane dye and is the monosodium salt of 4-[4-(N-ethyl-p-sulfoniumbenzylamino) diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Suitable humectants in the present invention include glycerin, propylene glycol, polyethylene glycol, sorbitan, fructose, mixtures thereof and the like. Humectants, when employed, may be present in amounts from about 10% to about 20%, by weight of the liquid oral antiseptic composition.

Suitable buffers in the present invention include citric acid-sodium citrate, phosphoric acid-sodium phosphate, and acetic acid-sodium acetate in amounts up to about 1%, and preferably from about 0.05% to about 0.5%, by weight of the liquid oral antiseptic composition.

The present invention extends to methods of making the improved liquid oral antiseptic compositions. The final compositions are readily prepared using methods generally known by those skilled in the dental art. In such a method, an oral antiseptic composition is made by first dissolving the surfactant in water, then admixing sorbitol or sorbitol solution to the surfactant solution until the sorbitol is dissolved. Coloring agents, additional sweetening agents, and similar additives are admixed at the same time sorbitol is added. The hexahydro-5-pyrimidinamine compound and thymol are then admixed to the surfactant/sorbitol solution until dissolved. The pH value of the solution is adjusted to 5-6 using IN hydrochloric acid or IN sodium hydroxide. Then sufficient water or alcohol, or mixtures thereof are added to the solution with mixing until the final solution volume is reached. In a preferred embodiment, the hexahydro-5-pyrimidinamine compound and thymol are added to the solution as the final ingredient.

The apparatus useful in accordance with the present invention comprises mixing apparatus well known in the dental art, and therefore the selection of the specific apparatus will be apparent to the artisan.

In another form of the invention, the oral antiseptic composition includes an oral vehicle and is in the form of a dental gel. As used herein, the term "gel" means a solid or semisolid colloid which contains considerable quantities of water. The colloid particles in a gel are linked together in a coherent meshwork which immobilizes the water contained inside the meshwork.

The maximum amount of hexahydro-5-pyrimidinamine compound which can be present in a dental gel is related to the solubility of the hexahydro-5-pyrimidinamine compound in the oral vehicle employed. In general, a dental gel will contain, in percentages by weight, from about 0.05% to about 0.3% of a hexahydro-5-pyrimidinamine compound, with about 0.2% being preferred.

In the dental gel compositions, the oral vehicle generally comprises water, typically in an amount from about 10% to about 90%, by weight of the dental gel composition. Polyethylene glycol, propylene glycol, glycerin, sorbitol or mixtures thereof may also be present in the vehicle as humectants or binders in amounts from about 18% to about 30%, by weight of the dental gel composition. Particularly preferred oral vehicles comprise mixtures of water with polyethylene glycol or water with glycerin and polypropylene glycol.

The dental gels of the present invention include a gelling agent (thickening agent) such as a natural or synthetic gum. Gelling agents such as hydroxyethyl cellulose, methyl cellulose and the like may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may contain the conventional additives set out above for mouthwash and spray antiseptic compositions and, in addition, may contain additional conventional additives such as a polishing agent, a desensitizing agent, a preservative and the like, providing the additives do not interfere with the antiseptic properties of the hexahydro-5-pyrimidinamine compound. The sorbitol solution, surfactants, fluorine providing compounds, sweetening agents, flavoring agents, coloring agents, humectants, buffers set out above as useful in the mouthwash and spray liquid oral antiseptic compositions may also be utilized in the dental gel compositions.

In addition to the anionic, nonionic, amphoteric and cationic surfactants which have been set out above as useful in the mouthwash and spray antiseptic compositions, the dental gel compositions may also contain a zwitterionic surfactant. These zwitterionic surfactants, when employed in the dental gel, may be present in amounts up to about 5%, and preferably from about 0.05% to about 2%, by weight of the dental gel composition.

Zwitterionic surfactants include the betaines and sulfobetaines. Typical alkyl dimethyl betaines include decyl betaine or 2-(N-decyl-N,N-dimethylammonio)acetate, coco betaine, myristyl betaine, palmityl betaine, lauryl betaine, cetyl betaine, stearyl betaine and the like. The amidobetaines similarly include cocoamidoethyl betaine, cocoamidopropyl betaine, lauramidopropyl betaine and the like. These sulfobetaines are similar in structure to the betaines, but have a sulfonate group in place of the carboxylate group and include alkylsulfobetaines, alkylamidosulfobetaines and alkylaminosulfobetaines.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 1%, by weight, and sodium citrate may be used in an amount from about 0.3% to about 9%, and preferably from about 0.6% to about 3%, by weight of the dental gel composition.

Suitable preservatives in the present invention include butylated hydroxyanisole (BHA), butylated hydroxytoluene (BHT), benzoic acid, ascorbic acid, methyl paraben, propyl paraben, tocopherols and mixtures thereof. Preservatives when used are generally present in amounts up to about 1.0%, and preferably from about 0.1% to about 1.0%, by weight of the dental gel composition.

The present invention extends to methods of making the improved liquid oral antiseptic compositions. The final compositions are readily prepared using methods generally known by those skilled in the dental art. In such a method, an antiseptic dental gel is made by first dispersing a gelling agent in a liquid (humectant and/or water), then admixing to the dispersion an aqueous solution of the water-soluble additives such as the fluorine providing compound, sweeteners and the like, then adding the polishing agent, and lastly admixing the surfactant, the flavoring agent, and the synergistic antiseptic composition containing the hexahydro-5-pyrimidinamine compound and thymol. The final gel mixture is then tubed or otherwise packaged. The liquids and solids in a gel product are proportioned to form a creamy or gelled mass which is extrudable from a pressurized container or from a collapsible tube.

The apparatus useful in accordance with the present invention comprises mixing apparatus well known in the dental art, and therefore the selection of the specific apparatus will be apparent to the artisan.

An important aspect of the present invention includes a hard or soft confectionery composition incorporating the inventive synergistic antiseptic composition and a method for preparing the hard or soft confections. In this form of the invention, the oral antiseptic composition includes a pharmaceutically acceptable carrier such as a confectionery bulking agent, the inventive synergistic antiseptic composition, and various additives. The confectionery may be in the form of a lozenge, tablet, toffee, nougat, suspension, chewy candy, chewing gum and the like. The pharmaceutically acceptable carriers may be prepared from a wide range of materials. Without being limited thereto, such materials include diluents, binders and adhesives, lubricants, disintegrants, coloring agents, bulking agents, flavoring agents, sweetening agents and miscellaneous materials such as buffers and adsorbents in order to prepare a particular antiseptic confection.

The preparation of confectionery formulations is historically well known and has changed little through the years. Confectionery items have been classified as either "hard" confectionery or "soft" confectionery. The synergistic antiseptic compositions of the present invention can be incorporated into confectionery compositions by admixing the inventive composition into conventional hard and soft confections.

As used herein, the term confectionery material means a product containing a bulking agent selected from a wide variety of materials such as sugar, corn syrup, and in the case of sugarless bulking agents, sugar alcohols such as sorbitol and mannitol and mixtures thereof. Confectionery material may include such exemplary substances as lozenges, tablets, toffee, nougat, suspensions, chewy candy, chewing gum and the like. The bulking agent is present in a quantity sufficient to bring the total amount of composition to 100%. In general, the bulking agent will be present in amounts up to about 99.98%, preferably in amounts up to about 99.9%, and more preferably in amounts up to about 99%, by weight of the oral antiseptic composition.

Lozenges are flavored medicated dosage forms intended to be sucked and held in the mouth. Lozenges may be in the form of various shapes such as flat, circular, octagonal and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and cooking continued until a final temperature of 145 to 156° C is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° to 170° C. in a few minutes. The candy is then rapidly cooled to 100° to 120° C. and worked as a plastic-like mass enabling incorporation of the additives, such as flavors, colorants and the like.

In vacuum cookers, the carbohydrate bulking agent is boiled to 125° to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from 4 to 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets*, Volume 1 (1980), Marcel Dekker, Inc., N.Y., N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agent, coloring agents, preservatives, medicaments, mixtures thereof and the like may be added thereafter also under agitation. A general discussion of the composition and preparation of nougat confections may be found in B. W. Minifie, *Chocolate, Cocoa and Confectionery: Science and Technology*, 2nd edition, AVI Publishing Co., Inc., Westport, Conn. (1980), at pages 424-425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The oral antiseptic compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as benzoic acid, sorbic acid, methyl paraben, and propyl paraben. Preservatives are generally present in amounts up to about 1%, and preferably from about 0.05 to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carageenans like alginic acid and its derivatives, xanthan gums, gelatin, acacis, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These colorants are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10%, and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the synergistic antiseptic composition with the thickener-water admixture to form a uniform thickener-synergistic antiseptic composition;

(D) combine the sweetener solution with the thickener-synergistic antiseptic composition and mix until uniform; and (E) admix the optional adjunct materials such as coloring agents, flavoring agents, decolorants, solubilizers, antifoaming agents, buffers and additional water with the mixture of step (D) to form the suspension.

The oral antiseptic compositions of this invention may also be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable antiseptic candy is prepared by procedures similar to those used to make soft confectionery. In a typical procedure, a boiled sugarcorn syrup blend is formed to which is added a frappe mixture. The boiled sugar-corn syrup blend may be prepared from sugar and corn syrup blended in parts by weight ratio of about 90:10 to about 10:90. The sugarcorn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The synergistic antiseptic composition of the instant invention can then be added to the homogeneous mixture as the temperature is lowered to about 65°–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, *Pharmaceutical Dosage Forms: Tablets* Volume 1, Marcel Dekker, Inc., N.Y., N.Y. at pages 289 to 466, which disclosure is incorporated herein by reference.

In accordance with this invention, therapeutically effective amounts of the synergistic antiseptic compositions of the present invention may be admixed into the hard and soft confections. These amounts are readily determined by those skilled in the art without the need for undue experimentation. In a preferred embodiment, the oral antiseptic hard and soft confection compositions comprise in percentages by weight (1) a hexahydro-5-pyrimidinamine compound in an amount from about 0.01% to about 0.3%, and (2) thymol in an amount from about 0.01% to about 0.4%. In a more preferred embodiment, the oral antiseptic hard and soft confection compositions comprise in percentages by weight (1) a hexahydro-5-pyrimidinamine compound in an amount from about 0.05% to about 0.2%, and (2) thymol in an amount from about 0.05% to about 0.1%. In a most preferred embodiment, the oral antiseptic hard and soft confection compositions comprise in percentages by weight (1) a hexahydro-5-pyrimidinamine compound in an amount from about 0.1% to about 0.15%, and (2) thymol in an amount from about 0.06% to about 0.08%. The pharmaceutically acceptable carrier is present in a quantity sufficient to bring the total amount of composition to 100%. The pharmaceutically acceptable carrier is preferably present in amounts up to about 99.98%, more preferably in amounts up to about 99.9%, and most preferably in amounts up to about 99%, by weight of the oral antiseptic hard and soft confection composition.

The present invention extends to methods of making the improved oral antiseptic hard and soft confection compositions. The synergistic antiseptic compositions may be incorporated into an otherwise conventional hard or soft confection compositions using standard techniques and equipment known to those skilled in the art.

Another important aspect of the present invention includes an oral antiseptic chewing gum composition incorporating the inventive synergistic antiseptic composition and a method for preparing the chewing gum composition, including both chewing gum and bubble gum formulations. In this form of the invention, the chewing gum composition contains a gum base, the inventive synergistic antiseptic composition, and various additives.

The gum base employed will vary greatly depending upon various factors such as the type of base desired, the consistency of gum desired and the other components used in the composition to make the final chewing gum product. The gum base may be any water-insoluble gum base known in the art, and includes those gum bases utilized for chewing gums and bubble gums. Illustrative examples of suitable polymers in gum bases include both natural and synthetic elastomers and rubbers. For example, those polymers which are suitable as gum bases include, without limitation, substances of vegetable origin such as chicle, crown gum, nispero, rosadinha, jelutong, perillo, niger gutta, tunu, balata, gutta-percha, lechi-capsi, sorva, gutta kay, mixtures thereof and the like. Synthetic elastomers such as butadiene-styrene copolymers, polyisobutylene, isobutylene-isoprene copolymers, polyethylene, mixtures thereof and the like are particularly useful.

The gum base may include a non-toxic vinyl polymer, such as polyvinyl acetate and its partial hydrolysate, polyvinyl alcohol, and mixtures thereof. When utilized, the molecular weight of the vinyl polymer may range from about 3,000 up to and including about 94,000.

The amount of gum base employed will vary greatly depending upon various factors such as the type of base used, the consistency of the gum desired and the other components used in the composition to make the final chewing gum product. In general, the gum base will be present in amounts from about 5% to about 94%, by weight of the final chewing gum composition, and preferably in amounts from about 15% to about 45%, and more preferably in amounts from about 15% to about 35%, and most preferably in amounts from about 20% to about 30%, by weight of the final chewing gum composition.

The gum base composition may contain conventional elastomer solvents to aid in softening the elastomer base component. Such elastomer solvents may comprise terpinene resins such as polymers of alphapinene or beta-pinene, methyl, glycerol or pentaerythritol esters of rosins or modified rosins and gums, such as hydrogenated, dimerized or polymerized rosins or mixtures thereof. Examples of elastomer solvents suitable for use herein include the pentaerythritol ester of partially hydrogenated wood or gum rosin, the pentaerythritol ester of wood or gum rosin, the glycerol ester of wood rosin, the glycerol ester of partially dimerized wood or gum rosin, the glycerol ester of polymerized wood or gum rosin, the glycerol ester of tall oil rosin, the glycerol ester of wood or gum rosin and the partially hydrogenated wood or gum rosin and the partially hydrogenated methyl ester of wood or rosin, mixtures thereof, and the like. The elastomer solvent may be employed in amounts from about 5.0% to about 75.0%, by weight of the gum base, and preferably from about 45.0% to about 70.0%, by weight of the gum base.

A variety of traditional ingredients may be included in the gum base in effective amounts such as plasticizers or softeners such as lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, mixtures thereof, and the like may also be incorporated into the gum base to obtain a variety of desirable textures and consistency properties. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like may also be incorporated into the gum base to obtain a variety of desirable textures and consistency properties. These traditional additional materials are generally employed in amounts up to about 30.0%, by weight of the gum base, and preferably in amounts from about 3% to about 20%, by weight of the gum base.

The gum base may include effective amounts of mineral adjuvants such as calcium carbonate, magnesium carbonate, alumina, aluminum hydroxide, aluminum silicate, talc, tricalcium phosphate, dicalcium phosphate and the like as well as mixtures thereof. These mineral adjuvants may serve as fillers and textural agents. These fillers or adjuvants may be used in the gum base in various amounts. Preferably the amount of filler when used will be present in an amount from greater than about 0% to about 60%, by weight of the chewing gum base.

The chewing gum base may additionally include the conventional additives of coloring agents, antioxidants, preservatives and the like. For example, titanium dioxide and other dyes suitable for food, drug and cosmetic applications, known as F.D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the chewing gum base.

The gum composition may include effective amounts of conventional additives selected from the group consisting of sweetening agents (sweeteners), plasticizers, softeners, emulsifiers, waxes, fillers, bulking agents, mineral adjuvants, flavoring agents (flavors, flavorings), coloring agents (colorants, colorings), antioxidants, acidulants, thickeners, mixtures thereof and the like. Some of these additives may serve more than one purpose. For example, in sugarless gum compositions, the sweetener, e.g., sorbitol or other sugar alcohol or mixtures thereof, may also function as a bulking agent. Similarly, in sugar containing gum compositions, the sugar sweetener can also function as a bulking agent.

The plasticizers, softeners, mineral adjuvants, colorants, waxes and antioxidants discussed above as being suitable for use in the gum base may also be used in the gum composition. Examples of other conventional additives which may be used include emulsifiers, such as lecithin and glyceryl monostearate, thickeners, used alone or in combination with other softeners, such as methyl cellulose, alginates, carrrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants. The fillers when used may be utilized in an amount from greater than about 0% to about 60%, by weight of the gum composition.

Bulking agents (carriers, extenders) suitable for use include sweetening agents selected from the group consisting of monosaccharides, disaccharides, polysaccharides, sugar alcohols, and mixtures thereof; polydextrose; maltodextrins; minerals, such as calcium carbonate, talc, titanium dioxide, dicalcium phosphate, and the like. Bulking agents may be used in amounts up to about 90%, by weight of the final gum composition, with amounts from about 40% to about 70%, by weight of the gum composition being preferred, with from about 50% to about 65%, by weight, being more preferred and from about 55% to about 60%, by weight of the chewing gum composition, being most preferred.

The sweetening agent used may be selected from a wide range of materials including water-soluble sweeteners, water-soluble artificial sweeteners, watersoluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as monosaccharides, disaccharides and polysaccharides such as xylose, ribulose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), known, for example, under the product designation of Sucralose; and (e) protein based sweeteners such as thaumaoccous danielli (Thaumatin I and II).

In general, an effective amount of sweetener is utilized to provide the level of bulk and/or sweetness desired, and this amount will vary with the sweetener selected. This amount of sweetener will normally be present in amounts from about 0.0025% to about 90%, by weight of the gum composition, depending upon the sweetener used. The exact range of amounts for each type of sweetener is well known in the art and is not the subject of the present invention. The amount of sweetener ordinarily necessary to achieve the desired level of sweetness is independent from the flavor level achieved from flavor oils.

Preferred sugar based-sweeteners are sugar (sucrose), corn syrup and mixtures thereof. Preferred sugarless sweeteners are the sugar alcohols, artificial sweeteners, dipeptide based sweeteners and mixtures thereof. Preferably, sugar alcohols are used in the sugarless compositions because these sweeteners can be used in amounts which are sufficient to provide bulk as well as the desired level of sweetness. Preferred sugar alcohols are selected from the group consisting of sorbitol, xylitol, maltitol, mannitol, and mixtures thereof. More preferably, sorbitol or a mixture of sorbitol and mannitol is utilized. The gamma form of sorbitol is preferred. An artificial sweetener or dipeptide based sweetener is preferably added to the gum compositions which contain sugar alcohols.

The coloring agents useful in the present invention are used in amounts effective to produce the desired color. These coloring agents include pigments which may be incorporated in amounts up to about 6%, by weight of the gum composition. A preferred pigment, titanium dioxide, may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F. D. & C. Blue No.2, which is the disodium salt of 5,5-indigotindisulfonic acid. Similarly, the dye known as F. D. & C. Green No.1 comprises a triphenylmethane dye and is the monosodium salt of 4-[4-(N-ethyl-p-sulfoniumbenzylamino) diphenylmethylene]-[1-(N-ethyl-N-p-sulfoniumbenzyl)-delta-2,5-cyclohexadieneimine]. A full recitation of all F. D. & C. colorants and their corresponding chemical structures may be found in the Kirk-Othmer Encyclopedia of Chemical Technology, 3rd Edition, in volume 5 at pages 857–884, which text is incorporated herein by reference.

Suitable oils and fats usable in gum compositions include partially hydrogenated vegetable or animal fats, such as coconut oil, palm kernel oil, beef tallow, lard, and the like. These ingredients when used are generally present in amounts up to about 7.0%, by weight, and preferably up to about 3.5%, by weight of the gum composition.

The synergistic antiseptic compositions may be incorporated into an otherwise conventional chewing gum composition using standard techniques and equipment known to those skilled in the art. For example, a gum base is heated to a temperature sufficiently high enough to soften the base without adversely effecting the physical and chemical make up of the base. The optimum temperatures utilized may vary depending upon the composition of the gum base used, but such temperatures are readily determined by those skilled in the art without undue experimentation.

The gum base is conventionally melted at temperatures that range from about 60° C. to about 120° C. for a period of time sufficient to render the base molten. For example, the gum base may be heated under these conditions for a period of about thirty minutes just prior to being admixed incrementally with the remaining ingredients of the base such as the plasticizer, fillers, the bulking agent and/or sweeteners, the softener and coloring agents to plasticize the blend as well as to modulate the hardness, viscoelasticity and formability of the base. The chewing gum base is then blended with the synergistic antiseptic composition of the present invention which may have been previously blended with other traditional ingredients. Mixing is continued until a uniform mixture of gum composition is obtained. Thereafter the gum composition mixture may be formed into desirable chewing gum shapes.

In accordance with this invention, therapeutically effective amounts of the synergistic antiseptic composition of the present invention may be admixed into chewing gum products. These amounts are readily determined by those skilled in the art without the need for undue experimentation. In a preferred embodiment, the oral antiseptic chewing gum compositions comprise in percentages by weight (1) a hexahydro-5-pyrimidinamine compound in an amount from about 0.01% to about 0.3%, and (2) thymol in an amount from about 0.01% to about 0.4%. In a more preferred embodiment, the oral antiseptic chewing gum compositions comprise in percentages by weight (1) a hexahydro-5-pyrimidinamine compound in an amount from about 0.05% to about 0.2%, and (2) thymol in an amount from about 0.05% to about 0.1%. In a most preferred embodiment, the oral antiseptic chewing gum compositions comprise in percentages by weight (1) a hexahydro-5-pyrimidinamine compound in an amount from about 0.1% to about 0.15%, and (2) thymol in an amount from about 0.06% to about 0.08%. The gum base and optional additives are present in quantities sufficient to bring the total amount of composition to 100%.

The present invention extends to methods of making the improved oral antiseptic chewing gum compositions. The synergistic antiseptic compositions may be incorporated into an otherwise conventional chewing gum composition using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

The kill curve data were calculated essentially according to the procedures described in *Antibiotics in Laboratory Medicine*, V. Lorian (Editor) 1980, Chapter 11, "Combinations of Antibiotics, Mechanisms of Interaction Against Bacteria," by D. J. Krogstad and R. C. Moellering, Williams & Wilkins, Baltimore/London.

In graph format kill curve data illustrates the antimicrobial activity of hexetidine, thymol, and the combination of hexetidine and thymol on the organism Streptococcus mutans, A. T. T. C. accession number 25175. The kill curve kinetics are presented in colony forming units versus time (minutes) for the following compositions: water, 0.01% hexetidine, 0.05% thymol, and 0.01% hexetidine and 0.05% thymol. The kill curve data show that the combination of thymol and hexetidine at low concentrations (0.01-0.001%) possesses potent antimicrobial activity. Thymol alone and hexetidine alone at these concentrations do not exhibit significant antimicrobial activity. Accordingly, the combination of thymol and hexetidine possesses potent synergistic antimicrobial activity.

In graph format kill curve data illustrates the antimicrobial activity of hexetidine, and the combination of hexetidine with individual essential oils on the organism *Streptococcus mutans*, A. T. T. C. accession number 25175. The kill curve kinetics are presented in colony forming units versus time (minutes) for the following compositions: 0.01% hexetidine, 0.05% thymol with 0.01% hexetidine, 0.05% eucalyptol with 0.01% hexetidine, 0.05% menthol with 0.01% hexetidine, and 0.05% methyl salicylate with 0.01% hexetidine. The kill curve data show that the combination of thymol and hexetidine at low concentrations (0.01-0.001%) possesses potent antimicrobial activity. Hexetidine, eucalyptol and hexetidine, menthol and hexetidine, and methyl salicylate and hexetidine, at these concentrations, do not exhibit comparable antimicrobial activity. Accordingly, the combination of thymol and hexetidine possesses potent synergistic antimicrobial activity.

The present invention is further illustrated by the following examples which are not intended to limit the effective scope of the claims. All parts and percentages in the examples and throughout the specification and claims are by weight of the final composition unless otherwise specified.

EXAMPLE 1

Inventive Run 1

This example demonstrates a method for preparing an oral antiseptic product in the form of a mouthwash formulation according to the process of the present invention having the composition set out in Table 1.

TABLE 1

| INGREDIENT | PERCENT W/V |
|---|---|
| hexetidine | 0.1 |
| thymol | 0.05 |
| nonionic surfactant | 0.7 |
| sorbitol solution (70% solids) | 50.0 |
| ethanol (95% in water) | 10.0 |
| coloring agent | 0.0004 |
| flavoring agent | 0.15 |
| deionized water | q.s. to 100.00 |

The above ingredients are admixed to form a solution. Hexetidine and thymol are added last to the surfactant/sorbitol solution and mixed until dissolved. The pH value of the solution is adjusted to 5-6 using 1N hydrochloric acid or 1N sodium hydroxide. Then sufficient water is added to the solution with mixing until the final solution volume is reached (q.s.-quantity sufficient to bring the total composition to 100%).

EXAMPLE 2

Inventive Run 2

This example demonstrates a method for preparing an oral antiseptic product in the form of an oral spray formulation according to the process of the present invention having the composition set out in Table 2.

TABLE 2

| INGREDIENT | PERCENT W/V |
|---|---|
| hexetidine | 0.2 |
| thymol | 0.1 |
| nonionic surfactant | 1.2 |
| citric acid; hydrous | 0.07 |
| ethanol (95% in water) | 12.0 |
| glycerol | 20.0 |
| sweetening agent | 0.01 |
| flavoring agent | 0.1 |
| deionized water | q.s to 100.00 |

The oral spray formulation is prepared essentially according to the procedure described in example 1. The oral spray formulation is combined with an appropriate propellant during the packaging step.

EXAMPLE 3

Inventive Run 3

This example demonstrates a method for preparing an oral antiseptic product in the form of a troche (lozenge) formulation according to the process of the present invention having the synergistic antiseptic composition set out in Table 3.

TABLE 3

| INGREDIENT | PERCENT W/V |
|---|---|
| hexetidine | 0.2 |
| thymol | 0.1 |
| flavoring agent | 0.2 |
| bulking agent | 99 |
| deionized water | q.s. to 100.00 |

The above ingredients are admixed into the confectionery bulking agent.

EXAMPLE 4

Inventive Run 4

This example demonstrates a method for preparing an oral antiseptic product in the form of a gel formulation according to the process of the present invention having the composition set out in Table 4.

TABLE 4

| INGREDIENT | PERCENT W/V |
|---|---|
| hexetidine | 0.2 |
| thymol | 0.1 |
| methyl cellulose | 2.0 |
| sorbitol solution (70% solids) | 50.0 |
| flavoring agent | 0.2 |
| deionized water | q.s. to 100.00 |

The above ingredients are admixed to form a gel. Hexetidine and thymol are added last to the gel and mixed until dissolved. The pH value of the gel is adjusted to 5-6 using 1N hydrochloric acid or 1N sodium hydroxide. Then sufficient water is added to the gel with mixing until the final solution volume is reached. The final gel mixture is then tubed or otherwise packaged.

The invention being thus described, it will be obvious that the same may be varied in many ways. Such variations are not to be regarded as a departure from the spirit and scope of the invention and all such modifications are intended to be included within the scope of the following claims.

We claim:

1. An oral antiseptic composition which comprises a therapeutically effective amount of a synergistic antiseptic composition comprising in combination from about 0.01% to about 0.2% by weight of an antiseptic hexahydro-5-pyrimidinamine compound and from about 0.05% to about 0.1% by weight thymol in an oral vehicle.

2. The oral antiseptic composition according to claim wherein the antiseptic hexahydro-5-pyrimidinamine compound is selected from the group consisting of hexetidine, pharmaceutically acceptable salts of hexetidine, and mixtures thereof.

3. The oral antiseptic composition according to claim 1 wherein the amount of hexahydro-5-pyrimidinamine compound present is in the range from about 0.05% to about 0.2%, by weight of the oral antiseptic composition.

4. The oral antiseptic composition according to claim 3 wherein the amount of hexahydro-5-pyrimidinamine compound present is in the range from about 0.1% to about 0.15%, by weight of the oral antiseptic composition.

5. The oral antiseptic composition according to claim 1 wherein the amount of thymol present is in the range from about 0.06% to about 0.08%, by weight of the oral antiseptic composition.

6. The oral antiseptic composition according to claim 1 wherein the oral vehicle is water.

7. The oral antiseptic composition according to claim 1 wherein the oral vehicle is an alcohol-water mixture.

8. The oral antiseptic composition according to claim 1 in the form of a mouth wash, oral spray, or dental gel.

9. The oral antiseptic composition according to claim 1 which further comprises an additive selected from the group consisting of sorbitol, a surfactant, a fluorine providing compound, a sweetening agent, a flavoring agent, a coloring agent, a humectant, a buffer, a gelling agent, a polishing agent, a desensitizing agent and a preservative.

10. A method for preparing an oral antiseptic composition which comprises admixing a therapeutically effective amount of a synergistic antiseptic composition comprising in combination from about 0.01% to about 0.2% by weight of an antiseptic hexahydro-5-pyrimidinamine compound and from about 0.05% to about 0.1% by weight thymol in an oral vehicle.

11. An oral antiseptic composition which comprises a therapeutically effective amount of a synergistic antiseptic composition comprising in combination from about 0.01% to about 0.2% by weight of an antiseptic hexahydro-5-pyrimidinamine compound and from about 0.05% to about 0.1% by weight thymol in a pharmaceutically acceptable carrier.

12. The oral antiseptic composition according to claim 11 wherein the antiseptic hexahydro-5-pyrimidinamine compound is selected from the group consisting of hexetidine, pharmaceutically acceptable salts of hexetidine, and mixtures thereof.

13. The oral antiseptic composition according to claim 11 wherein the amount of hexahydro-5-pyrimidinamine compound present is in the range from about 0.05% to about 0.2%, by weight of the oral antiseptic composition.

14. The oral antiseptic composition according to claim 13 wherein the amount of hexahydro-5-pyrimidinamine compound present is in the range from about 0.1% to about 0.15%, by weight of the oral antiseptic composition.

15. The oral antiseptic composition according to claim 11 wherein the amount of thymol present is in the range from about 0.05% to about 0.08%, by weight of the oral antiseptic composition.

* * * * *